(12) United States Patent
Thomas et al.

(10) Patent No.: US 9,775,940 B2
(45) Date of Patent: Oct. 3, 2017

(54) METHOD AND APPARATUS FOR MITIGATING ACUTE REOXYGENATION INJURY DURING PERCUTANEOUS CORONARY INTERVENTION

(71) Applicant: Rheoxtech, LLC, Chicago, IL (US)

(72) Inventors: Neil J. Thomas, Chicago, IL (US); Gintaras A. Vaisnys, Chicago, IL (US)

(73) Assignee: Rheoxtech, LLC, Chicago, IL (US)

( * ) Notice: Subject to any disclaimer, the term of this patent is extended or adjusted under 35 U.S.C. 154(b) by 0 days.

(21) Appl. No.: 15/362,307

(22) Filed: Nov. 28, 2016

(65) Prior Publication Data

US 2017/0072127 A1 Mar. 16, 2017

Related U.S. Application Data

(63) Continuation of application No. 14/802,340, filed on Jul. 17, 2015, now Pat. No. 9,504,779, which is a
(Continued)

(51) Int. Cl.
*A61M 31/00* (2006.01)
*A61M 1/36* (2006.01)
(Continued)

(52) U.S. Cl.
CPC ........ *A61M 1/3613* (2014.02); *A61M 1/1698* (2013.01); *A61M 1/32* (2013.01);
(Continued)

(58) Field of Classification Search
CPC .... A61M 1/36; A61M 1/3666; A61M 5/1723; A61M 1/3613; A61M 2001/3613
(Continued)

(56) References Cited

U.S. PATENT DOCUMENTS 4,466,804 A 8/1984 Hino
4,493,692 A 1/1985 Reed
(Continued)

FOREIGN PATENT DOCUMENTS

EP 0357338 A2 3/1990
FR 2513884 A 4/1983
(Continued)

OTHER PUBLICATIONS

Supplementary Partial European Search Report dated Feb. 20, 2007.
(Continued)

*Primary Examiner* — Jason Flick
(74) *Attorney, Agent, or Firm* — King & Spalding LLP

(57) ABSTRACT

A system and methods are described for improving the management of ischemic cardiac tissue during acute coronary syndromes. The system combines a catheter-based sub-system which allows for simultaneous balloon dilation of a coronary artery and infusion of a carefully controlled perfusate during percutaneous coronary intervention. The system allows for modulation of levels of oxygen at the time of percutaneous intervention. In addition, catheters and systems are provided for administration of fluids with modified oxygen content during an intervention that incorporate upstream flow control members to compartmentalize the perfusion of the target coronary artery and the remainder of the heart.

19 Claims, 4 Drawing Sheets

Related U.S. Application Data continuation of application No. 14/039,673, filed on Sep. 27, 2013, now Pat. No. 9,084,856, which is a continuation of application No. 12/505,309, filed on Jul. 17, 2009, now Pat. No. 8,562,585.

(60) Provisional application No. 61/081,450, filed on Jul. 17, 2008.

(51) Int. Cl.
*A61M 1/32* (2006.01)
*A61M 25/10* (2013.01)
*A61M 5/172* (2006.01)
*A61M 1/16* (2006.01)

(52) U.S. Cl.
CPC ............ *A61M 1/36* (2013.01); *A61M 1/3666* (2013.01); *A61M 5/1723* (2013.01); *A61M 25/10* (2013.01); *A61M 25/104* (2013.01); *A61M 2025/1095* (2013.01); *A61M 2202/0439* (2013.01); *A61M 2205/3306* (2013.01); *A61M 2205/3375* (2013.01); *A61M 2230/005* (2013.01); *A61M 2230/205* (2013.01)

(58) Field of Classification Search
USPC .......................................................... 604/66
See application file for complete search history.

(56) References Cited

U.S. PATENT DOCUMENTS

| | | |
|---|---|---|
| 4,540,399 A | 9/1985 | Litzie et al. |
| 5,011,469 A | 4/1991 | Buckberg et al. |
| 5,322,500 A | 6/1994 | Johnson et al. |
| 5,725,492 A | 3/1998 | Igo et al. |
| 5,770,073 A | 6/1998 | Bach et al. |
| 5,895,578 A | 4/1999 | Simard et al. |
| 5,935,093 A | 8/1999 | Elgas et al. |
| 6,039,078 A | 3/2000 | Tamari |
| 6,071,258 A | 6/2000 | Dalke et al. |
| 6,248,087 B1 | 6/2001 | Spears et al. |
| 6,387,323 B1 | 5/2002 | Afzal et al. |
| 6,443,609 B2 | 9/2002 | Short |
| 6,454,999 B1 | 9/2002 | Farhangnia et al. |
| 6,607,698 B1 | 8/2003 | Spears et al. |
| 6,613,008 B2 | 9/2003 | Aboul-Hosn et al. |
| 6,730,267 B2 | 5/2004 | Stringer et al. |
| 6,746,417 B2 | 6/2004 | Spears et al. |
| 6,918,887 B1 | 7/2005 | Gremel et al. |
| 6,974,435 B2 | 12/2005 | Daw et al. |
| 7,022,099 B2 | 4/2006 | Litzie et al. |
| 7,131,963 B1 | 11/2006 | Hyde |
| 7,455,812 B2 | 11/2008 | Thomas |
| 2002/0085952 A1 | 7/2002 | Ellingbee et al. |
| 2003/0023230 A1* | 1/2003 | Lewis .................... A61B 17/22 604/537 |
| 2005/0063860 A1 | 3/2005 | Carpenter et al. |
| 2005/0084416 A1* | 4/2005 | Thomas .............. A61M 1/3621 422/45 |
| 2005/0154344 A1 | 7/2005 | Chang |
| 2006/0258981 A1 | 11/2006 | Eidenschink |
| 2007/0041909 A1 | 2/2007 | Kupussamy et al. |
| 2008/0171726 A1 | 7/2008 | Roth et al. |

FOREIGN PATENT DOCUMENTS

| | | |
|---|---|---|
| FR | 2648714 A1 | 12/1990 |
| WO | WO 99/08733 | 2/1999 |
| WO | WO 99/08734 A1 | 2/1999 |
| WO | WO 00/16825 A1 | 3/2000 |
| WO | WO 00/47266 | 8/2000 |
| WO | WO 03/070300 | 8/2003 |

OTHER PUBLICATIONS

Thomas, N. "Controlled Cardiac Reoxygenation in Adults with Ischemic Heart Disease,", The Journal of Thoracic and Cardiovascular Surger, Mar. 1999.

Ihnken et al., "Normoxic Cardiopulmonary Bypass Reduces Oxidative Myocardial Damage and Nitric Oxide During Cardiac Operations in the Adult," Cardiovascular Surgery, 1998, vol. 116, No. 2.

Ihnken et al., "Delayed Cardioplegic Reoxygenation Reduces Reoxygenation Injury in Cyanotic Immature Hearts," The Society of Thoracic Surgeons, 1998.

Allen et al., "Detrimental Effects of Cardiopulmonary Bypass in Cyanotic Infants: Preventing the Reoxygenation Injury," The Society of Thoracic Surgeons, 1997.

\* cited by examiner

METHOD AND APPARATUS FOR MITIGATING ACUTE REOXYGENATION INJURY DURING PERCUTANEOUS CORONARY INTERVENTION

CROSS-REFERENCE TO RELATED APPLICATIONS

This application is a continuation of and claims priority to U.S. patent application Ser. No. 14/802,340, filed Jul. 17, 2015, and titled "Method and Apparatus for Mitigating Acute Reoxygenation Injury During Percutaneous Coronary Intervention," which is a continuation of and claims priority to U.S. patent application Ser. No. 14/039,673, filed Sep. 27, 2013, and titled "Method and Apparatus for Mitigating Acute Reoxygenation Injury During Percutaneous Coronary Intervention," which is now U.S. Pat. No. 9,084,856 issued Jul. 21, 2015, and which is a continuation of and claims priority to U.S. patent application Ser. No. 12/505,309, filed Jul. 17, 2009, and titled "Method and Apparatus for Mitigating Acute Reoxygenation Injury During Percutaneous Coronary Intervention," which is now U.S. Pat. No. 8,562,585 issued Oct. 22, 2013, and which claims priority to U.S. Provisional Application No. 61/081,450, filed Jul. 17, 2008. The disclosure of each of the foregoing applications is hereby incorporated by reference in its entirety.

FIELD OF THE INVENTION

The invention relates to the clinical arena of interventional cardiology and, in particular, the field of percutaneous coronary interventions and treatments for acute coronary syndrome (acute myocardial infarction and/or unstable angina). A method and apparatus is described that provides the operator with an ability to mitigate oxygen-related injury to a tissue by precisely modulating the level of oxygen re-exposure of the tissue at and directly after the time of the intervention. Specific catheters and systems for administration of fluids with modified oxygen content during angioplasty procedures are also provided.

BACKGROUND

Considerable effort and resources have been devoted to reducing the burden of cardiovascular disease and mortality rates after acute myocardial infarction have decreased over the past 30 years. However, coronary artery disease remains the leading cause of morbidity and mortality in the developed world. An estimated 79.4 million American adults (1 in 3) have one or more types of cardiovascular disease. Of these, an estimated 1.4 million Americans per year will have a myocardial infarction and another 500,000 present with other forms of acute coronary events that lead to cardiac ischemia. In 2007, an estimated 1.68 million patients were discharged in the US suffering from acute coronary syndrome. In 2004, an estimated 6,363,000 in-patient cardiovascular operations and procedures were performed in the United States. These included an estimated 1,285,000 in-patient angioplasty procedures, 427,000 in-patient bypass procedures and 1,471,000 in-patient diagnostic cardiac catheterizations (see Rosamond et al. (2007) Heart Disease and Stroke Statistics—2007 Update. *Circulation.* 115:e69-e171).

For patients who suffer from any form of acute coronary event, the heart muscle is deprived of adequate levels of oxygen for a variable period of time and along a range of severity until appropriate treatment can be initiated. In many cases, irreversible damage to the heart can result in infarction, with cell death occurring in one of more areas of the left ventricular or right ventricular myocardium or within the conduction system of the heart. In addition to the effects of this lack of available oxygen on cardiomyocytes and conduction tissue, it has become increasingly recognized that the endothelial cells lining the blood vessels (down to the capillary level) can also be damaged or can become impaired in their ability to function even downstream from the immediate infarction.

For patients with acute coronary thrombosis and infarction, established therapy is timely reperfusion of the culprit coronary artery by opening or bypassing the artery and restoring blood flow to the ischemic territory. Modern treatment of acute myocardial infarction or myocardial ischemia usually comprises performing balloon angioplasty with or without stent deployment, directional atherectomy with or without distal protection or even laser therapy and intracoronary declotting. Such procedures can all be broadly considered to be part of the clinical arena of percutaneous coronary intervention (PCI). Both percutaneous intervention and surgical bypass of the vessels to facilitate increased blood flow are performed to "salvage" myocardium or other cardiac tissue at risk from further damage by ongoing ischemia that may result in an extension of infarction or new areas of damage. During what could be defined as the "reperfusion era" it has been observed that reestablishing proper flow into epicardial coronary arteries: (i) mitigates injury if it is performed in a timely fashion; and (ii) improves survival in large cohorts of patients presenting with the clinical syndrome of myocardial infarction. Simultaneously, however, it has been observed that in certain circumstances, especially in cases of protracted or severe ischemia, reintroduction of blood flow and oxygen can ramp up the injury in a manner consistent with what has been described as reperfusion injury.

In the last several decades, considerable effort has focused on limiting infarct size and other manifestations of post-ischemic injury. The concepts of ischemic pre- and post-conditioning suggest highly evolved mechanisms by which the heart can protect itself from ischemia under certain conditions and further investigation points to intracellular signaling mechanisms that can mitigate injury. In addition, the last decade has allowed for a broader understanding of the membrane-bound ionic pump disturbances that develop as ischemia progresses and the resultant ionic membrane shifts that are involved in the development of post-ischemic contracture when the affected tissue is re-exposed to oxygen containing blood. These disturbances may also point to mechanisms of conduction system dysfunction and/or post-ischemic arrhythmias.

Numerous methods of reducing ischemic insults to tissue, such as through interventional catheters that allow infusion of the patient's own oxygenated blood, have been contemplated. For example, U.S. Pat. No. 5,403,274 by Cannon provides an apparatus for passively perfusing blood past a stenosis using pressure equalization. U.S. Pat. Nos. 5,573,508 and 5,573,509 by Thornton, assigned to Advanced Cardiovascular Systems (ACS), are directed to an intravascular catheter with a perfusion lumen that can be expanded to increase the flow of oxygenated blood or other body fluids when the distal portion of the catheter is occluded. U.S. Pat. No. 5,308,356 by Blackshear provides a passive perfusion catheter with a balloon that defines at least one passage to permit blood flow when the balloon is pressed against the wall of the blood vessel. Similarly, U.S. Pat. No. 5,505,702 by Arney, assigned to Scimed Life Systems provides a dilation catheter with a composite balloon that allows passive blood flow past the catheter during dilation. U.S. Pat. No. 5,344,402 provides a low profile drug delivery catheter with at least one port to permit perfusion of the upstream blood while the drug delivery balloon is inflated. U.S. Pat. No. 6,302,865 provides a guidewire with a perfusion lumen allowing for perfusion of the arterial blood past an inflated balloon.

To increase blood flow and reduce ischemia, active perfusion catheters have also been provided that allow perfusion of high oxygen content fluids past an infarct area. U.S. Pat. No. 5,137,513 by McInnes, assigned to ACS, provides a catheter and method of 'active' perfusion, wherein oxygenated blood, preferably from the upstream artery is supplied during inflation of a balloon. Similarly, U.S. Pat. No. 5,807,331 by den Heiher and Solar, assigned to Cordis Corp., provides an active perfusion catheter where blood or other high oxygen content fluids are perfused past the obstruction during balloon inflation.

Higher oxygen replacement has also been contemplated. For example, European Patent No. 0836495 provides an apparatus for delivering oxygen-supersaturated solutions during clinical procedures such as angioplasty. Recent clinical trials on such systems have failed to show any significant benefit from the use of supersaturated oxygen therapy. Similarly, U.S. Pat. No. 6,454,997 by Divino et al., assigned to Therox, Inc. provides a high oxygen content fluid through a catheter in an attempt to reduce ischemic injury by combining an oxygen-supersaturated fluid with patient blood. U.S. Pat. No. 5,186,713 by Raible, assigned to Baxter International, Inc. provides a method and device for the flow of oxygenated perfusion fluid, preferably the patient's blood, by active perfusion through an oxygenator.

Although there have been significant advances in reducing ischemia, a major area of focus has become reducing or even preventing injury that occurs after a rapid return of normal blood flow. Typically, coronary intervention after acute MI involves percutaneous transluminal coronary angioplasty either with or without subsequent stent deployment. After a short episode of myocardial ischemia, reperfusion of the area with the patient's blood results in the rapid restoration of cellular metabolism and function. In clinical situations in which ischemia is more protracted or severe, even with the successful treatment of occluded vessels and stenting a serious risk of heart dysfunction and even death still exists. If the ischemic episode has been of sufficient severity or duration, reperfusion may, paradoxically, result in a worsening of heart function.

Reperfusion injury occurs in tissue when blood supplies return to the tissue after a period of ischemia. The absence of oxygen and nutrients from blood creates a condition in which the subsequent restoration of circulation results in inflammation and oxidative damage through the induction of oxidative stress rather than restoration of normal function. This damage is distinct from the injury resulting from the ischemia per se. Reperfusion injury may be due in part to the inflammatory response of damaged tissues involving the production of reactive oxygen species, resulting in: damage to lipid bilayer cellular membranes; endothelial cell dysfunction; micro-vascular injury; alterations in intracellular $Ca^{2+}$, sodium, potassium and hydrogen ion homeostasis; changes in myocardial metabolism; and activation of neutrophils, platelets, and the complement system. In addition, white blood cells carried to the area by newly returning blood cause the release of a host of inflammatory cytokines and other factors such as interleukins as well as free radicals in response to tissue damage. Under certain conditions, therefore, the restoration of blood flow to ischemic tissue exposes the tissue to levels of oxygen that can be damaging.

Several efforts have been made to reduce reperfusion injuries after PCI. For example, U.S. Publication No. 2006/0258981 by Eidenschink provides a catheter that will reduce the temperature of the surrounding tissue to minimize post-reperfusion injuries. U.S. Publication No. 2006/0100639 provides a method and apparatus for treatment of reperfusion injury by altering blood flow or oxygen delivery after reperfusion of the infarct.

What has typically been overlooked is the possibility of avoiding reoxygenation injury altogether by controlling oxygen deliver during the initial maneuvers. There remains a need to provide a reliable method of preventing post-angioplasty reoxygenation injury.

SUMMARY OF THE INVENTION

In keeping with the foregoing discussion of the molecular mechanisms, it is known that reoxygenation injury can occur after reestablishing blood flow (perfusion) to a previously ischemic tissue. It has not been widely appreciated that the severity (intensity and duration) of the antecedent ischemic conditions sets the stage for significant oxygen-related damage depending upon certain conditions that exist at the moment flow is reestablished or ischemia is eliminated. Furthermore, it has not been appreciated that even a brief period of abrupt oxygen re-exposure to ischemic tissue, can initiate damaging oxidative stress, result in numerous inflammatory and gene-related processes and lead to increased injury due to ionic imbalances that develop during the ischemic period. Key calcium ion fluctuations or oscillations triggered by the presence of molecular oxygen that lead to various degrees of contracture can also occur. These consequences may be mitigated by avoiding exposure of the tissue at risk to hyperoxygenated (or even relatively hyperoxic) perfusates, which create large tissue oxygen gradients. High oxygen gradients have been observed to create a consistent pattern of injury during the initial phase of reperfusion/reoxygenation. As such, in one embodiment of the invention, a method of preventing reoxygenation injury during acute PCI is provided comprising administering a modulated oxygen content fluid during and immediately upon re-opening of an occluded blood vessel in a patient undergoing a coronary intervention. In particular, the modulated oxygen content fluid has an initial oxygen content below that of normal arterial blood. This is specifically contrasted to any strategy whereby the procedure to open the vessel occurs first, is completed, and is followed by an attempt to alleviate the damage already caused by abrupt reestablishment of adequate flow to alleviate ischemic conditions. In one specific embodiment, the coronary intervention is balloon angioplasty and, in particular, it is contemplated to provide an angioplasty catheter with an infusion lumen that is connected to a system that provides inflow of a perfusate containing gradually increasing levels of oxygen during the procedure. During this procedure, oxygen delivery to the tissue being treated is guided by a protocol for oxygen reentry that is ramped or increased as a function of time.

A method is provided of treating a patient undergoing a intervention procedure in which blood flow to a tissue has been reduced comprising providing a catheter comprising an infusion lumen wherein the infusion lumen is designed so as to provide infusion of a fluid to a tissue distal to an occlusion; inserting the catheter into a blood vessel in which blood flow has been reduced; and infusing a modulated oxygen content fluid through the infusion lumen wherein the fluid comprises an oxygen concentration that is controlled over time, wherein normal blood flow is not reestablished to the tissue before the infusion. In specific embodiments, the oxygen concentration of the fluid is increased over time. In specific embodiments, the oxygen concentration of the fluid is initially lower than the oxygen concentration of blood in the affected artery, and specifically is lower than a normal oxygen content of arterial blood.

Furthermore, consistent with a strategy of avoiding any exposure of the tissue at risk to even relatively hyperoxic perfusate, in another specific embodiment a method is provided wherein, during the intervention, an upstream occluding member is attached to a guide catheter that occludes or blocks the inflow of unmodified blood into the target artery to facilitate controlled reoxygenation. Such precise perfusion is then externally managed via a perfusion device to facilitate precise operator control of the oxygen partial pressure of the perfusate. During such a procedure, an angioplasty catheter including an infusion lumen is threaded into a patient's artery, typically using a guidewire and through the introducing lumen of the previously described guide catheter. After the balloon is advanced through the vessel narrowing, the balloon is inflated against the blockage. Prior to or at the precise moment of inflation of the balloon, the modulated oxygen content fluid administration begins to the patient. In some embodiments, the balloon is inflated prior to administration of a modulated oxygen content fluid. In certain other embodiments, a fluid is administered prior to inflation of the balloon, in particular a low oxygen content fluid that can be more consistent with the pre-existent condition of the tissues in question. In this manner, no highly oxygenated blood is allowed to perfuse the ischemic tissue and initiate reoxygenation injury, oxidative stress, and explosive oxygen radical formation, membrane damage in the form of peroxidation of lipid bilayers, deranged calcium flux, contracture or the resultant release of inflammatory mediators in response to said injury. As the oxygen gradient is ramped gradually as a function of time, additional time is provided for restoration of more appropriate ionic positioning (at the cell membrane and/or within the sarcoplasmic reticular membrane).

In certain embodiments, the partial pressure of oxygen is raised gradually as a function of time and from as low as 20-30 mmHg of oxygen to physiologic oxygen tension of from 60-110 mmHg (or possibly higher) over a period of time that approximates 15-20 minutes. These parameters are intended to be illustrative rather than limiting. The modulated oxygen perfusate can be administered through an angioplasty catheter or a guide catheter with an upstream occluding member from between about five to about twenty minutes depending of the severity of the pre-existent ischemic conditions. This time frame may be modified to determine the most appropriate oxygen modulation curve (oxygen partial pressure as a function of time). The ranges and the time frame given are used for illustrative purposes and are not intended to be limiting.

In certain embodiments, the modulated oxygen content fluid is a mixture of arterial and venous blood and can also include crystalloid solution. In certain embodiments, the mixture is of blood taken from the patient and re-circulated. In some embodiments, the blood is initially venous blood. In some embodiments, arterial blood is added to the venous blood to result in various ratios of venous (deoxygenated) to arterial (oxygenated) blood in a time frame consistent with that stated above starting from the time of the initial balloon inflation or just prior upon engaging the target artery. In certain other embodiments, the ratio of arterial blood is increased in a stepwise fashion so that, at the end of a specified time frame, only arterial (oxygenated) blood is administered. In some embodiments, the degree of oxygenation of arterial blood is increased steadily as a function of time so that only arterial blood is administered but with a gradually increasing oxygen partial pressure.

In certain embodiments, the method further comprises placing an oxygen sensor distal to the catheter to ensure the accuracy of the oxygen delivery. In certain embodiments, the oxygen sensor can be on a guidewire. In certain other embodiments, the catheter additionally comprises an oxygen sensor at the distal tip of the balloon. In certain embodiments, the sensors are not in the patient's body but are external, for example as part of the oxygenation system.

In some embodiments, the oxygen content of the fluid is modulated by use of an oxygenator. In certain embodiments, the fluid is a low oxygen content fluid such as venous blood and the content of oxygen is increased, such as through an oxygenator. In some other embodiments, the oxygen content is regulated by at least one deoxygenator. In certain embodiments, the initial fluid is a high oxygen content fluid such as arterial blood and the content of oxygen is reduced.

In certain embodiments, the oxygenator is controlled by at least one microprocessor. In some embodiments, the oxygen content is modulated based on a preset program that may be overridden manually by the operator. In yet other embodiments, the oxygen content is controlled by the user. In certain other embodiments, at least one microprocessor receives data from oxygen sensors and adjusts a pump or an oxygenator or both to adjust the flow or oxygenation content of an infusion fluid and regulate the content of oxygen in the infusion fluid to correspond to a programmed set point.

In certain of these embodiments, a sensor provides a baseline reading of blood flow or oxygen content in the vessel that is used to generate initial parameters for oxygen content. In certain embodiments, the initial oxygen content in the infusion fluid is at or above the content of blood flow or oxygen measured prior to commencement of the PCI procedure. In certain other embodiments, the initial oxygen content in the fluid is at or below the content of oxygen measured prior to commencement of the PCI procedure. In certain other embodiments, the length of time of infusion of modulated oxygen content fluid is dependent on the level of blood flow or oxygen content of the infusion fluid as measured prior to commencement of the PCI procedure.

In certain embodiments, the oxygen content in the perfusate fluid is assigned based on the content of oxygen needed in the vessel, which can be provided by sensors that can provide a starting point for therapy. The oxygen content can be measured either by analyzing the partial pressure of oxygen in the blood, or by measuring the oxygen saturation of the patient's hemoglobin. In one non-limiting embodiment, the partial pressure of oxygen can be ramped up 1 mmHg at a time every 15-60 seconds and from approximately 20 mmHg to as high as 90-110 mmHg over a 5-20 minute time frame depending on initial conditions and/or the judgment of the operator.

In another embodiment a patient's blood may be rerouted to a heart lung machine, mini-heart lung machine or cardiopulmonary bypass circuit either with or without the capacity for an oxygenator or separate cardioplegia circuit. As such, wherein the heart's workload is diminished and therefore the minute-to-minute oxygen demand of the heart is limited, these maneuvers may also effect changes in the overall supply-demand balance of oxygen to the heart and may, by itself, limit or eliminate the ischemic conditions.

In some embodiments, the sensor measures the oxygen content of a location distal to the catheter, such as the coronary sinus. In other embodiments, the sensor measures oxygen content of a location not distal to the catheter. In certain embodiments, a ratio of oxygen content in blood distal to and not distal, especially proximal, to the catheter is measured and that ratio provides the basis for setting the initial oxygen content in the perfusion fluid and may suggest alterations in ideal time frame of the change in oxygen as a function of time or may prompt a change in the starting point for the partial pressure of oxygen in the initial perfusate.

In still other non-limiting embodiments, parameters other than oxygen are not modulated over time. The temperature of the fluid can be at normal physiologic body temperature of the patient (normothermic). In certain non-limiting embodiments, the procedure is conducted during PCI not associated with a cardiopulmonary bypass. In some embodiments, the procedure can be conducted without the patient's arterial blood being rerouted from the body. In specific embodiments, the patient has a functioning heart and lungs. Typically, a cardioplegia solution is not administered to the tissue before balloon inflation.

In some embodiments, the fluid is infused directly through a pump that can be free-standing from any extracorporeal circuit. In other embodiments, the fluid is infused from a reservoir that may be integrated into a cardiopulmonary bypass circuit. In certain embodiments, the pump is regulated by a controller. The controller can be programmable. In certain embodiments, the controller sets infusion parameters based on measurement of a patient parameter.

In certain embodiments, the balloon completely occludes blood flow in the artery. The balloon is typically inflated only once, and no arterial blood is initially allowed to pass beyond the balloon. In some embodiments, the catheter includes only a single balloon.

The method can further comprise inserting a stent into the artery. The stent can be inserted after infusion of the modified oxygen perfusate. In another embodiment the stent is inserted prior to the infusion of the modified oxygen perfusate. As such the stent can be positioned on the balloon and inserted during dilatation and infusion of the modified oxygen perfusate. In another embodiment the stent is positioned on a second catheter and not deployed until after the controlled reoxygenation is completed. In another embodiment, the infusion is before placement of a stent. The stent can thus be inserted after arterial blood has been reintroduced into the area distal to the catheter but not before the operator has had the opportunity to perform the controlled oxygen procedure for the purpose of rescuing the tissue at risk.

In particular embodiments of the invention, the host or subject to which the method and system is applied is a human. In specific embodiments, the host is a human who is in need of prevention of reoxygenation injury. In certain embodiments, the host is a human patient with cardiovascular disease.

DETAILED DESCRIPTION

Figure 4:
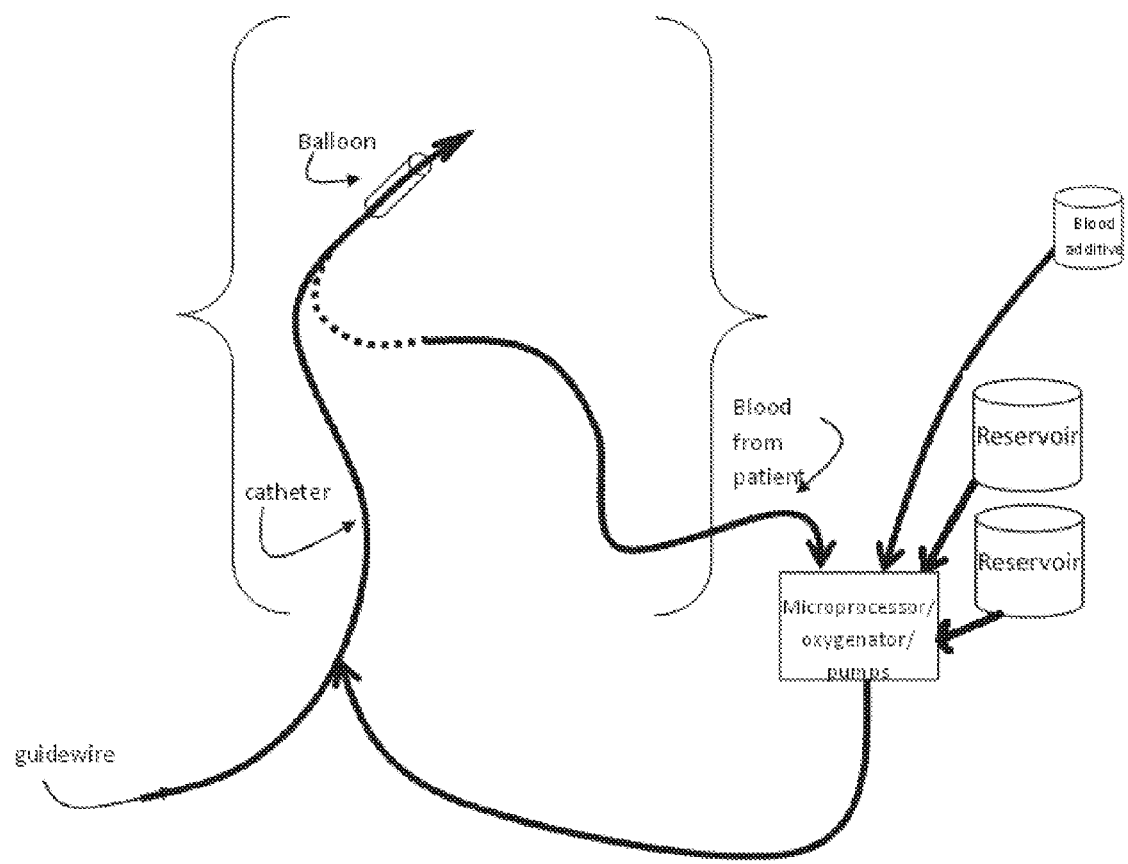
FIG. 4 is a diagram of a perfusion catheter system that can be used for the invention.

In a first exemplary embodiment a method of preventing post-PCI reoxygenation injury is provided comprising administering a modulated oxygen content perfusate during the intervention. The method can be used for performing a percutaneous coronary intervention during an acute coronary syndrome or myocardial infarction in which it is recognized that a variable degree of ischemia is present. In particular embodiments, the method can be used when it is recognized that the ischemic tissue must be managed carefully and attended to differently than in more elective interventions. The invention can be used either during an acute coronary event or in conjunction with PCI related to a chronic obstruction. In specific embodiments, the coronary intervention may be percutaneous transluminal coronary balloon angioplasty (a type of PCI), coronary atherectomy and/or deployment of a coronary stent. As shown in FIG. 4 in particular, it is contemplated to provide an angioplasty catheter with an infusion lumen that is connected to a system that provides inflow of an increasing content of oxygen during the angioplasty procedure.

In a typical PCI procedure, the physician uses local anesthetic to numb a specific area of the patient's body, usually the upper thigh area where the femoral artery is located. A small tube called a sheath is inserted into an artery, such as the femoral artery. A flexible balloon-tipped plastic catheter approximately 2 mm in diameter and 80 cm long is inserted through the sheath, advanced to the heart and directed to an area of coronary blood vessel narrowing. The balloon mounted on the tip of the catheter is introduced into the coronary artery until it traverses the thrombus and/or occlusion. The balloon is inflated to a pressure of typically 6-8 atmospheres. The balloon expands and enlarges the artery by compressing the thrombus material and/or plaque and opening the coronary artery. For an artery having a 3 mm nominal diameter, the balloon is expanded to 2.7 to 3.3 mm diameter by inflation to a "nominal" balloon pressure. The inflation of the balloon is actuated by a control console that is external to the patient and connected to the catheter. Manufacturers of angioplasty balloons supply pressure vs. diameter compliance curves to physicians. When the balloon inflates, it displaces the blockage against the vessel wall and reopens the vessel. The same catheter that is used to open the occluded coronary artery is used to control blood flow to the distal branches of the coronary artery and the zone of infarct. With the blood flow restored, the balloon catheter is then deflated and removed.

It is conventional during acute PCI (PCI performed during an acute coronary event) that after the inflation of the balloon, the physician rapidly deflates the balloon and removes it from the coronary artery quickly to allow blood flow to the distal coronary branches and to the zone of the heart muscle that may already have infarcted areas (non-contracting, necrotic tissue that will be replaced by scar tissue) and tissue that is not yet infarcted but is ischemic and at risk of infarct. In the prior art, such perfusion with unmodified blood after the abrupt opening of an obstruction rushes to the tissue at risk of infarction and may cause reperfusion injury with a component of reoxygenation injury; depending upon the antecedent ischemic conditions.

Similarly, coronary artery stenting is a catheter-based procedure in which a stent (a small, expandable wire mesh tube or scaffolding) is inserted into a diseased artery to hold open the artery. Its most common use is in conjunction with balloon angioplasty to treat coronary artery disease. After the angioplasty balloon reduces the narrowing of the coronary artery, the stent is inserted to prevent the artery from re-closing. Stents are left in place in the artery. In the setting of an acute MI and acute PCI, angioplasty pre-dilatation is always performed before stenting. In this exemplary embodiment the balloon pre-dilatation is linked by way of a specialized flow catheter to provide a controlled oxygen content perfusate prior to stent deployment.

In one embodiment, a balloon tipped catheter may be used both as an angioplasty dilation balloon and to provide a modulated oxygen content fluid to the area distal to the catheter during the procedure. The balloon can be, for example, positioned inside the narrowed or occluded coronary vessel at the site of the coronary lesion. At the time the balloon is inflated a concomitant interruption of already diminished blood flow in the coronary artery supplying the heart muscle at risk of reoxygenation injury occurs. In the prior art this was viewed primarily as an issue leading to a brief period of additional ischemia. However, this invention mitigates over-exposure to abrupt oxygen gradients and reduces injury by allowing for immediate initiation of carefully controlled blood flow with a modified oxygen content fluid.

Figure 1:
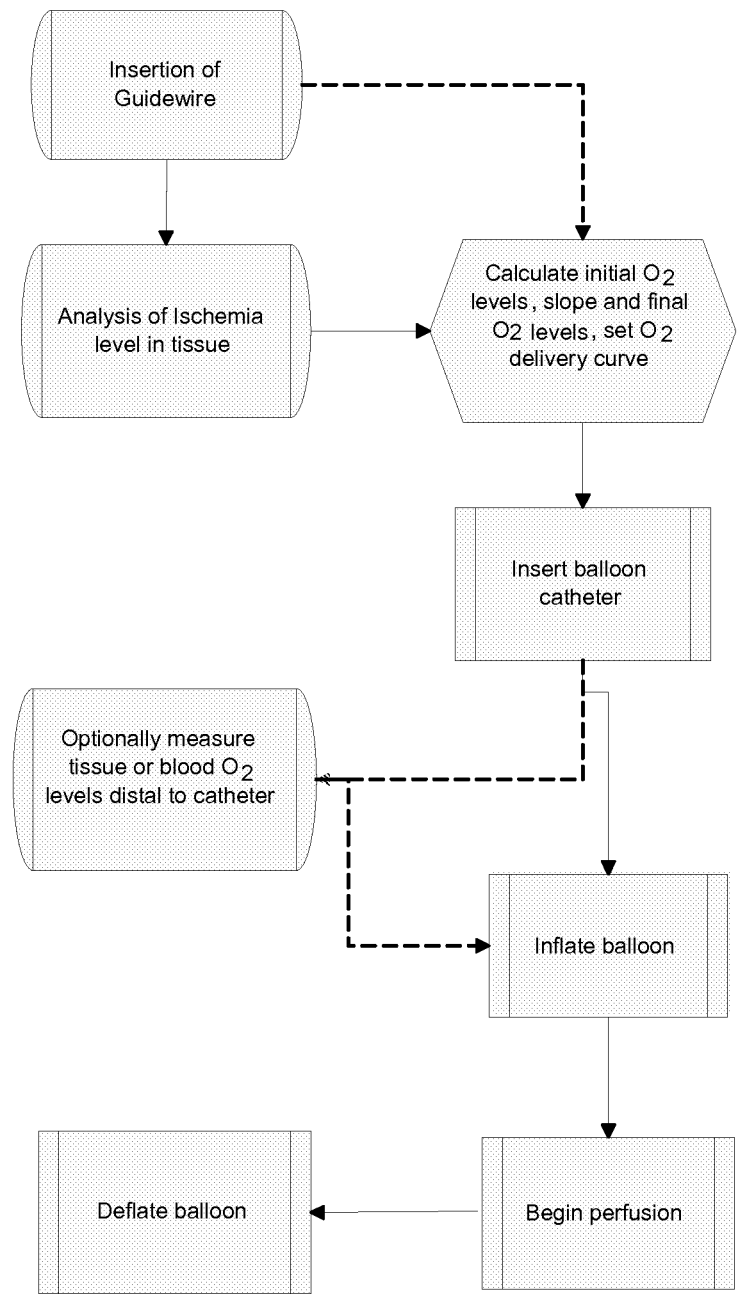
FIG. 1 is a schematic of the method of the invention.

An embodiment of a process of the invention is shown in FIG. 1. The physician inserts a guidewire into the artery past the blockage. The guidewire tip can either include a probe or sensor that can measure oxygen content, or the physician can already have used other means to assess the extent of ischemia in the area. In certain instances, the physician cannot appropriately assess the level of ischemia and must base the content of oxygen and fluid levels to be given to the patient based on a standard model. In either case, an oxygen curve is calculated for the patient that includes the starting content of oxygen in the perfusate, the final levels, the time course over which the content will be increased and whether this will be in a stepwise, linear, curvilinear or smooth fashion. These examples are provided to be illustrative rather than limiting. After analysis of the oxygen content of the fluid and calculation of the oxygen curve, a balloon catheter is inserted over the guidewire. At this stage it may be beneficial to measure oxygen content distal to the balloon to refine the initial setup of the oxygen delivery curve. After the final oxygen delivery curve is calculated, the balloon is inflated and perfusion with the modulated oxygen content fluid is begun. After the oxygen perfusion curve is finalized, the balloon is deflated and the catheter removed.

Modulated Oxygen Content Fluid

The invention provides prevention of reoxygenation injury specifically by modulating the exposure of the ischemic tissue to oxygen during acute percutaneous coronary intervention. In contrast, the prior art envisioned allowing arterial and relatively hyperoxic blood to perfuse the distal artery after ischemia for at least some period of time prior to infusing a modified fluid.

A modulated oxygen content fluid is one in which the fluid comprises an oxygen partial pressure or oxygen concentration that changes over time. In particular embodiments, the oxygen content of the fluid is increased over time. The oxygen level or concentration can increase gradually, or increase in graduated steps. In certain embodiments the amount of oxygen does not rise steadily, but at times either remains constant or is lowered, for example to accommodate the needs of the patient. The modulated oxygen content fluid can be blood or can be any other physiologically acceptable solution, such as a supplemented saline, blood plasma, lactate solution, Ringer's solution, venous blood, a mixture of deoxygenated, such as venous and oxygenated, such as arterial blood, or a mixture of blood and a suitable physiologic solution similar in composition to blood plasma, water, a cardioplegia crystalloid solution, or other buffered solution. In certain embodiments, the modulated oxygen content fluid is not made by mixing deoxygenated and oxygenated blood. In this embodiment, the fluid can be oxygenated blood or a blood substitute mixed with a low-oxygen blood additive. The fluid can also be blood that is oxygenated to the desired oxygen content.

In some embodiments, the modulated oxygen content fluid flows through the vascular system passively, through a pressure gradient. In other embodiments, the fluid is actively perfused by a pump, the fluid flow rate of which can be varied.

In certain non-limiting embodiments, the oxygen content of the fluid is increased from 1% of the oxygen content of the arterial blood to 100% of the oxygen content of arterial blood over the course of the procedure. The procedure can be from one to sixty minutes or more. In some embodiments, the procedure is carried out over about sixty minutes or less, for example over about 40, about 30, about 20, about 15 or about 10 minutes. In other embodiments, the oxygen content is increased from 5% to 75% over the course of thirty minutes. In yet another non-limiting embodiment, the oxygen content is increased from 5 to 50% over the course of twenty minutes.

In certain non-limiting embodiments, oxygen content is increased in a stepwise fashion. For example, the modulated oxygen content fluid can, at time $t_0$ be less than 50% oxygen saturation, such as less than 20%. This level of oxygen can be perfused for a period of time to $t_1$. The first period can be about 15 minutes, or it can be less such as for example ten, nine, eight, seven, six, five or less minutes. At time $t_1$, the content of oxygen can be increased to about 50%, such as between 40 and 60% up until time $t_2$. The second period can be approximately 15 minutes, or can be less, such as for example ten, nine, eight, seven, six, five or less minutes. At time $t_2$, the content of oxygen can be increased to about 75%, such as between 60 and 80% up until time $t_3$. The third period can also be approximately 15 minutes, or can be less, such as for example ten, nine, eight, seven, six, five or less minutes. At time $t_3$, the content of oxygen can be increased to levels approximating arterial blood. In certain instances, at $t_3$, the balloon is deflated and arterial blood is allowed to perfuse the area.

Figure 2:
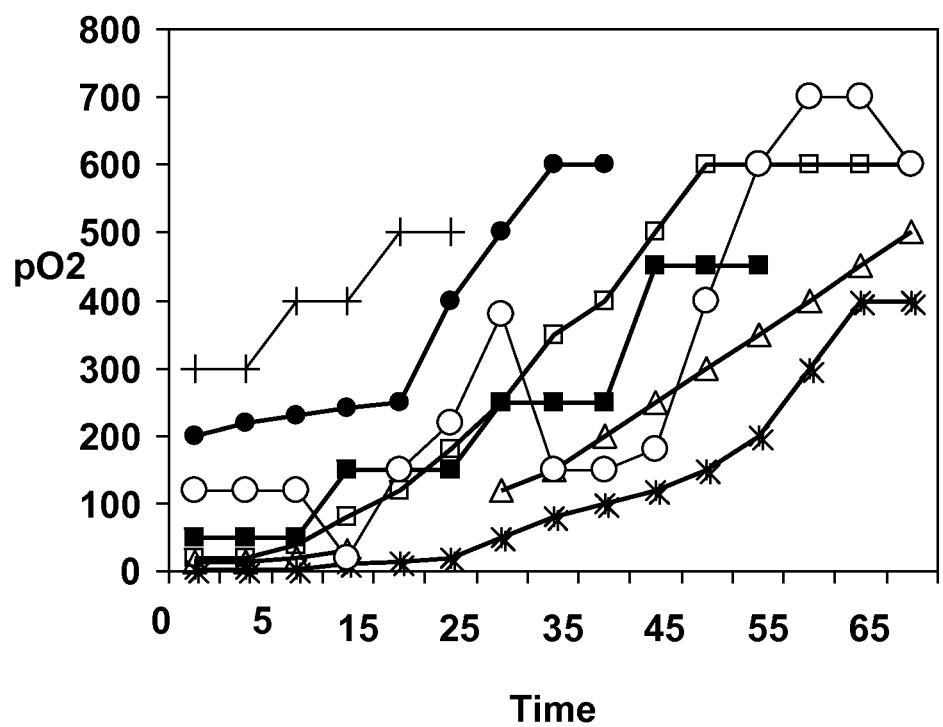
FIG. 2 provides a proposed oxygen delivery graph, based on different initial ischemia levels

Some illustrative embodiments of a modulated oxygen content administration curve are presented in FIG. 2. In embodiments, such as when ischemia is minor, very low levels of oxygen are not necessary for extended periods of time. In those instances, the initial curve can begin at approximately 20 mmHg and rapidly rise, for example within 5 minutes or less. In other instances, such as if ischemia is severe, low levels of oxygen should be provided for at least 5 or at least 10 minutes.

The balloon can be gradually deflated to gradually allow the flow of the normal arterial blood to be mixed with the oxygen poor perfusate coming out of the tip of the catheter. If the coronary artery is not occluded by the balloon at the end of therapy all the blood flow to the infarct zone will come from natural perfusion of the heart with arterial blood.

The perfusate in which oxygen is regulated can be leukocyte-depleted blood of the same patient or a donor. In one embodiment, blood will be removed from the patient, put though a filter that removes a significant portion of the leukocytes, in certain cases neutrophils, and then used to perfuse the area distal to the tip of the catheter. In one embodiment, blood may be withdrawn from the sheath used for arterial access but may be withdraw from the patient using any other method of arterial or venous access that will provide the desired blood flow for perfusion. The mode of withdrawal may be using gravity or a pump as long as the desired blood flow is achieved. The blood is then passed though a leukocyte-removal filter to remove a clinically advantageous amount of leukocytes from the blood. An example of one such filter is the Cellsorba-80P (Asahi Medical Co).

Oxygen content of the blood or perfusion fluid can be read by sensors that may take a variety of forms. For example, the oxygen content may comprise partial pressure of oxygen ($pO_2$) or the percentage of oxygen saturation ($O_2$ saturation). Alternatively, the sensors may measure both $pO_2$ and the $O_2$ saturation. In yet another embodiment, the coronary perfusion device addresses oxygen content by considering the total amount of oxygen content in the fluid. Any of these measurements for the purposes of the current application can be considered to represent an "oxygen content." In this regard, non-limiting alternative embodiments may evaluate oxygen content by evaluating $pO_2$, $O_2$ saturation, hemoglobin level, and/or the amount of oxygen dissolved in the blood.

As one skilled in the art would appreciate, the oxygenator may take several different forms. For example, the oxygenator may be a bubble or membrane oxygenator. Similarly, the pump may comprise a variety of different types of pumps. For example, a roller pump or centrifugal pump, in which the speed of the spinning head (and the resistance of the system) determines the flow of blood or perfusate, a piston-based arrangement that may affect flow by the application of pressure onto previously described bladder reservoirs, or any now known or later developed device suitable for controlling the flow of fluids may be used.

Typically, the content of oxygen is regulated in the circuit through an oxygenation controller. The oxygenation controller typically includes one or more selected from a microprocessor, a general processor, a controller, an application specific integrated circuit, a transistor, a field programmable gate array, an analog circuit, a digital circuit, valves, pumps, filters, tubing, a reservoir, a bladder, a series of reservoirs or bladders, relays, sensors, and pulse oximetry sensors, combinations thereof or other now known or later developed devices for mixing fluids from two different sources by using data relating to partial pressure of oxygen, oxygen saturation, or oxygen content in the fluids. In certain embodiments, the oxygenation controller regulates oxygen content based on a preset automatic or manually entered protocol.

The oxygenation controller allows the operator to adjust the oxygen content of the blood sent through the catheter. In one embodiment, the oxygenation controller includes a dial for adjusting the output oxygenation content and a real-time display for parameters such as oxygen saturation and partial pressure of oxygen ($pO_2$). In other embodiments, the oxygenation controller may include one or more of a variety of different input devices, including buttons, knobs, a mouse, a trackball, sliders, touch pads, sensors or touch screens, to control parameters of the output blood. The oxygenation controller can also be pre-set to run a particular protocol automatically. In some instances, the controller running a pre-set protocol can be regulated by external data such as data from sensors. In particular embodiments, the controller is automatically pre-set based on initial patient parameters (such as physical characteristics (height, weight, etc.), measured ischemia, clinical symptoms, or the like) but the protocol is automatically adjusted. In certain embodiments, the controller has pre-set a number of perfusion protocols that are automatically selected based on certain patient parameters, such as those above or others yet to be identified.

In some instances, the modulated oxygen content fluid is prepared by mixing oxygenated blood, which can be aortic or prepared by use of an oxygenator, with a physiologic fluid such as normal saline that contains no oxygen. In certain embodiments, the modulated oxygen content fluid is prepared using procedures such as described in U.S. Patent Application No. 2005/0084416, which is incorporated herein. A half blood-half saline mix will produce approximately 45-50% oxygen saturation in the perfusate. Mixing can be accomplished outside of the body or inside of the body by adding known amount of saline to the blood inside the targeted coronary artery. For example if blood flow in the coronary artery is 50 ml/min, infusing 25 ml/min of saline into the artery will result in approximately 50% reduction of oxygen delivery to the infarct zone. In some embodiments, the oxygenation controller mixes oxygenated and deoxygenated blood in a ratio that results in a controlled oxygen saturation and $pO_2$ level before delivery of the mixed blood through the catheter. In this embodiment, the oxygenation controller can include two inputs: an oxygenated blood input and deoxygenated blood input, which can come from the venous supply. The oxygenated blood input receives oxygenated blood directly or indirectly from the oxygenator. The oxygen partial pressure and saturation levels are measured by a sensor. The deoxygenated blood input directly or indirectly receives blood that was collected in the venous reservoir. The oxygen partial pressure and saturation levels of this blood are also measured by a sensor. A pump can control the flow of both oxygenated and deoxygenated blood to a reservoir.

Oxygen Content

In certain embodiments, the oxygen content in the fluid is controlled by at least one microprocessor. The microprocessor can receive data from sensors, pumps, and a perfusion control input. The microprocessor can be a digital signal processor, application specific integrated circuit, a field programmable gate array, a control processor, an analog circuit, a digital circuit, a network, combinations thereof or other now known or later developed device for controlling a mixing ratio.

Sensors can provide the microprocessor with data about the level of oxygen of the fluids being administered. In certain other embodiments, at least one microprocessor receives data from the sensors and controls pumps that adjust the flow of an oxygenated fluid to regulate the oxygen content in the infusion fluid.

The sensors can also provide information on parameters other than oxygen content. In one embodiment, the sensors provide information on levels of occlusion. This can be measured using, for example, ultrasound, Doppler, or pressure sensors, among others. In other embodiments, the sensors can provide information on additional blood constituents.

In some embodiments, an oxygen sensor is placed at the site of narrowing prior to placement of the catheter. In certain of these embodiments, the sensor provides a baseline reading that is used to generate initial parameters for oxygen content. In certain embodiments, the initial oxygen content is at or above the content of oxygen measured prior to commencement of the PCI procedure. In certain other embodiments, the initial oxygen content is at or below the level of oxygen measured prior to commencement of the PCI procedure. In certain other embodiments, the length of time of infusion of modulated oxygen content fluid is dependent on the level of oxygen measured prior to commencement of the PCI procedure.

In certain other embodiments, a sensor measures the level of occlusion of an artery prior to intervention. In certain embodiments, the percentage occlusion provides a baseline reading used to generate initial parameters for oxygen levels. In certain other embodiments, the level of occlusion is used to regulate the length of time of infusion of the modulated oxygen content fluid. In some embodiments, the level of occlusion is measured using ultrasound. In other embodiments, the level of occlusion is measured by Doppler flow. In still other embodiments, the occlusion is measured using a pressure sensor, such as a sensor or meter on the catheter.

Additionally, other sensors may be added to incorporate measurement of other parameters of the deoxygenated blood, oxygenated blood, modulated oxygen content fluid, or the overall mixture provided to the perfusion pathway. The sensors may be in a variety of locations. For example, sensors may be located in reservoirs, pumps, or tubing. A fewer number of sensors may be used, such as only one sensor at an output of the mix or two sensors at the two inputs without a sensor at the output.

In certain embodiments, the level of oxygen in the tissue is measured before perfusion and the oxygen content in the fluid is set based on the level of oxygen in the tissue. In furtherance of this embodiment, the partial pressure of oxygen provokes a microprocessor response that causes a gradual ramping up of the oxygen content in the perfusate over time. In certain embodiments, the oxygen content is measured by measuring the partial pressure of oxygen. In some embodiments, abrupt changes to the $pO_2$ and a gradient beyond 20 mmHg is not allowable for the first 20 minutes of the therapy. After the first twenty minutes the gradient is allowed to widen; however other embodiments provide for use of this device platform to perform research to further elucidate the optimal gradients and the optimal time frames and function curves of change of $pO_2$ as a function of time.

In some embodiments, the sensor measures the oxygen content of blood distal to the catheter. In other embodiments, the sensor measures oxygen content of blood not distal to the catheter. In certain embodiments, a ratio of oxygen levels in blood distal to and not distal, especially proximal, to the catheter is measured and that ratio provides the basis for setting the initial levels and infusion parameters of the perfusion fluid.

The sensors may be constructed using fiberoptics for oximetry readings, continuous blood gas analysis, or any other method in which blood chemistry levels, such as $pO_2$ or oxygen saturation, may be obtained. A perfusion control, such as a memory, processor, data base, user input device or a data port, allows a perfusionist to control the oxygen partial pressure and saturation levels. Typically, the microprocessor also includes a display. The perfusion control provides the microprocessor with the desired parameters. Utilizing the data received from the sensors, the microprocessor can control pumps regulating modulated oxygen content fluid to insure that the desired oxygen content of the output is achieved. The display is usually a monitor, CRT, LCD, projector, LED or other now known or later developed display device. The display may provide data on the input and output oxygen content, blood flow rates, pressure levels or combinations thereof.

Figure 3:
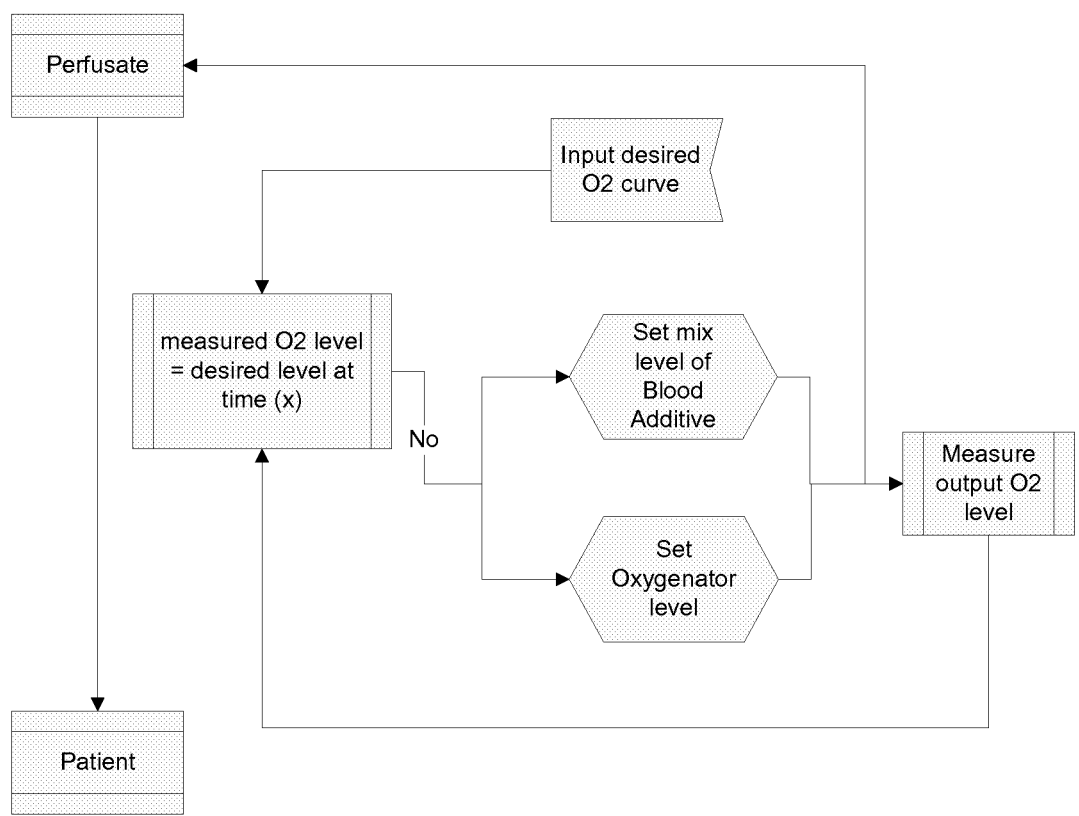
FIG. 3 is a schematic of a perfusion control apparatus for use in the invention.

One non-limiting embodiment of a mechanism by which the oxygen levels can be regulated is shown in FIG. 3. In this embodiment, the oxygen content in the blood or blood substitute as well as any blood additive (such as saline) are measured. These are compared to a desired blood input curve. If the levels of the perfusate are those desired, no further adjustments are made to the perfusate. If the levels do not match the desired level, the system adds oxygen through an oxygenator or deoxygenates the perfusate either through, for example, a filter or reduces oxygen concentration by dilution through addition of low oxygen content fluid such as saline, and mixes this modulated fluid into the perfusate reaching the patient until desired levels are achieved in the perfusate reaching the tissue.

In addition, catheters and systems are provided for administration of fluids with modified oxygen content during an intervention that incorporate upstream flow control members to compartmentalize the perfusion of the target coronary artery and the remainder of the heart. In certain embodiments, the flow control members limit the flow of arterial blood into a target blood vessel. In specific embodiments, the upstream flow control members regulate the flow of oxygen modulated fluid into the blood vessel distal to an occlusion. In specific embodiments, the flow control members limit the flow of hyperoxygenated fluid, including arterial blood, into hypoxic tissues, in particular into areas around the occlusion.

In yet another embodiment, the microprocessor may control a timing mechanism that gauges the time frame in which specific levels of oxygenation (or other parameters) occur. Alarm mechanisms may also be incorporated to send a warning to the perfusionists or operator concerning whether input or output blood levels are low, whether the oxygen content is too high or too low. The alarms can be controlled by the microprocessor based on the sensor or other information received and displayed on the display. Additionally, another microprocessor may control the operation of the oxygenation controller.

Types of Catheters

Typically an angioplasty catheter includes a perfusion lumen. The catheter can be any of a variety of perfusion catheters known in the art, such as those used to infuse drugs, blood and blood substitutes into the blood vessels of the heart. Suitable catheters include, for example, those described in U.S. Pat. No. 5,833,659, to Cordis, which describes an apparatus and method is disclosed relating to a rapid exchange perfusion and infusion balloon catheter for treating a blood vessel with a treatment fluid; U.S. Pat. No. 5,823,996 to Cordis, which provides an infusion catheter with a passageway in the catheter body extending to an infusion device which has inner and outer chambers with holes in a wall that route the solution into a subject vasculature; U.S. Pat. No. 5,403,274 by Cannon, which provides an apparatus for passively perfusing blood past a stenosis using pressure equalization; U.S. Pat. Nos. 6,302,865 and 5,797,876 to Spears, which provide guidewires with a perfusion lumen allowing for perfusion of the arterial blood past an inflated balloon; U.S. Pat. No. 5,137,513 by McInnes, assigned to ACS, which provides a catheter and method of 'active' perfusion; U.S. Pat. No. 5,807,331 by den Heiher and Solar, assigned to Cordis Corp., which provides an active perfusion catheter where fluids are perfused past the obstruction during balloon inflation; U.S. Pat. No. 5,318,531, which provides a balloon catheter in which the balloon comprises a plurality of holes to permit medication delivered through the lumen to pass outwardly through the holes; European Patent No. 0836495, which provides an apparatus for delivering oxygen-supersaturated solutions during clinical procedures such as angioplasty; U.S. Pat. No. 5,186,713 by Raible, assigned to Baxter International, Inc. provides a method and device for providing flow of oxygenated perfusion fluid, preferably the patient's blood, by active perfusion through an oxygenator; U.S. Publication No. 2006/0258981 by Eidenschink, which provides a catheter that will reduce the temperature of the surrounding tissue to minimize post-reperfusion injuries; and U.S. Publication No. 2006/0100639, which provides a method and apparatus for treatment of reperfusion injury by altering blood flow or oxygen delivery following reperfusion of the infarct.

A catheter can be equipped with a balloon used to isolate the distal section (branches) of the coronary artery that perfuse the infarct area. The perfusate is discharged from the distal end of the catheter. Standard perfusion means such as hydration or electronic IV infusion pumps, pressurized IV bags or motorized syringe fluid delivery systems, blood pumps such as cardioplegia pumps and heart lung bypass machines, or regulated systems such as those described herein above can be used to perfuse the infarct zone for up to 20 or up to 30 or up to 40 or up to 50 or up to 60 minutes following the opening of the artery. Typically, a perfusate flow of less than 100 ml/min will be sufficient.

In some embodiments, a perfusion catheter can be used which includes at least two balloons. In a non-limiting example of this use, both balloons are inflated. The distal balloon can thereafter be deflated to allow slow perfusion of the tissue distal to the occlusion. The perfusate is thereafter infused between the proximal and distal balloon.

This disclosure has been presented in the context of coronary interventions, however these techniques are equally applicable to non-coronary interventions such as peripheral interventions, brain-related interventions such as in cases of stroke or other cerebrovascular disorders, or any other interventions in which ischemic tissue will be exposed to oxygenated fluids.

It will be apparent to one of skill in the art that the embodiments provided are merely exemplary, and that the invention should not be so limited. Accordingly, those of skill in the art will recognize various alternative designs and embodiments for practicing the invention.

The invention claimed is:

1. A reperfusion system for use in treating a patient undergoing an interventional procedure in which a blood flow to a tissue has been reduced comprising:
   a catheter having a vascular occluding member and a lumen having an entrance and an exit wherein the vascular occluding member is positioned therebetween; and
   an oxygenation controller in fluid communication with the catheter, the oxygenation controller comprising:
   a pump for forcing a perfusate through the lumen;
   a perfusate oxygenation modulator for controlling an oxygen level within the perfusate, and
   a controller configured to change the oxygen level within the perfusate from a first oxygen level to at least a second oxygen level, the second oxygen level being different from the first oxygen level and having electronically stored therein a plurality of treatment protocols for tissues having various initial levels of ischemia, each treatment protocol defining an intentional change in oxygenation level over time of the perfusate for a tissue having a specific initial level of ischemia, and programming to select one of the electronically stored plurality of treatment protocols based on an inputted tissue's initial level of ischemia and to control the perfusate oxygenation modulator to render a selected treatment protocol.

2. The system of claim 1 further comprising an oxygen sensor in electrical communication with the controller.

3. The system of claim 1 wherein the controller controls the oxygen level in the perfusate from a 1% oxygen level to an oxygen level below the oxygen level of venous blood.

4. The system of claim 1, further comprising an oxygen sensor in electrical communication with the controller, the oxygen sensor sensing an actual oxygen level, the controller comparing the actual oxygen level to the instantaneous oxygenation level.

5. The system of claim 1, further comprising at least two reservoirs, each reservoir suitable for containing a perfusate component and connected to the pump, the oxygen level being regulated by selecting an appropriate ratio of perfusate components.

6. The system of claim 5, wherein at least one reservoir contains oxygen.

7. The system of claim 5, wherein the perfusate components can create a perfusate having an oxygen level less than that in arterial blood.

8. The system of claim 5, wherein the controller controls the pump such that the perfusate is pumped at a constant flow rate.

9. The system of claim 1, wherein the catheter is a balloon catheter.

10. The system of claim 1, wherein the controller includes a processor.

11. The system of claim 1, wherein the controller regulates the oxygen level in the perfusate from an oxygen level consistent with venous blood to an oxygen level consistent with arterial blood.

12. The controller of claim 1, wherein at least some of at least two reservoirs contain perfusate components suitable to create a perfusate having an oxygen level consistent with venous blood to an oxygen level consistent with arterial blood.

13. An oxygenation controller for use in treating a patient undergoing an interventional procedure in which a blood flow to a tissue has been reduced comprising:
   a pump for forcing a perfusate through a catheter having a vascular occluding member;
   a perfusate oxygenation modulator for controlling an oxygen level within the perfusate, and
   a controller configured to change the oxygen level within the perfusate from a first oxygen level to at least a second oxygen level, the second oxygen level being different from the first oxygen level and having electronically stored therein a plurality of treatment protocols for tissues having various initial levels of ischemia, each treatment protocol defining an intentional change in oxygenation level over time of the perfusate for a tissue having a specific initial level of ischemia, and programming to select one of the electronically stored plurality of treatment protocols based on an inputted tissue's initial level of ischemia and to control the perfusate oxygen modulator to render a selected treatment protocol.

14. The controller of claim 13, further comprising at least two reservoirs, each reservoir suitable for containing a perfusate component and connected to the pump, the oxygen level being regulated by selecting an appropriate ratio of the perfusate components.

15. The controller of claim 14, wherein at least one reservoir contains oxygen.

16. The controller of claim 13, further comprising at least two reservoirs, each reservoir containing a perfusate component suitable to create a perfusate having an oxygen level less than that in venous blood.

17. The controller of claim 13, further comprising at least two reservoirs, each reservoir containing a perfusate component suitable to create a perfusate having an oxygen level from less than 1% to an oxygen level below the oxygen level of venous blood.

18. The controller of claim 13, wherein the controller controls the pump such that the perfusate is pumped at a constant flow rate.

19. The controller of claim 13, wherein the controller includes a microprocessor.

* * * * *